United States Patent [19]

Chow et al.

[11] Patent Number: 4,587,361

[45] Date of Patent: May 6, 1986

[54] ANTHELMINTIC BENZAMIDES

[75] Inventors: Alfred W. Chow, Radnor; Vassilios J. Theodorides, West Chester, both of Pa.

[73] Assignee: SmithKline Beckman Corporation, Philadelphia, Pa.

[21] Appl. No.: 607,498

[22] Filed: May 7, 1984

[51] Int. Cl.[4] .................. C07C 103/26; C07C 67/02
[52] U.S. Cl. .................................... 564/179; 560/250;
[58] Field of Search .................... 564/179; 560/250; 514/617, 546

[56] References Cited

U.S. PATENT DOCUMENTS

| 3,674,849 | 7/1972 | Darlington et al. | 260/559 S |
| 3,801,637 | 4/1974 | Meek | 260/559 S |
| 3,839,443 | 10/1974 | Meek | 260/559 S |
| 4,435,418 | 3/1984 | Chow | 548/306 |

FOREIGN PATENT DOCUMENTS

| 2311229 | 9/1973 | Fed. Rep. of Germany | 564/179 |
| 1183641 | 3/1970 | United Kingdom | 564/179 |

*Primary Examiner*—Charles F. Warren
*Assistant Examiner*—R. A. Picard
*Attorney, Agent, or Firm*—Janice E. Williams; William H. Edgerton; Alan D. Lourie

[57] ABSTRACT

Flukicidal N-[4-(1-phenylethenyl)phenyl]-2-hydroxy-3,5-dihalobenzamides are prepared by reacting a halosalicylic acid with a 1-(4-aminophenyl)-1-phenylethylene in the presence of a halo condensing agent. A species of the invention is N-[4-(1-phenylethenyl)phenyl]-2-hydroxy-3,5-diiodobenzamide.

12 Claims, No Drawings

ANTHELMINTIC BENZAMIDES

This invention comprises a series of new benzamide compounds which have anthelmintic properties. More specifically, the compounds are N-[4-(1-phenylethenyl)-phenyl]-2-hydroxybenzamides which are active against internal parasites, especially flukes and nematodes, in man and animals.

BACKGROUND OF THE INVENTION

A number of prior patents describe variously substituted salicylanilides which have antimicrobial or anthelmintic properties. Representative of this art are U.S. Pat. Nos. 3,801,637, 3,674,849 and 3,839,443. U.S. Pat. No. 4,435,418 discloses certain phenylethenylbenzimidazoles which have anthelmintic activity. This art is believed not pertinent to the new compounds of the present invention based on the difference in their respective structures.

DESCRIPTION OF THE INVENTION

The compounds of this invention are illustrated by the following structural formula:

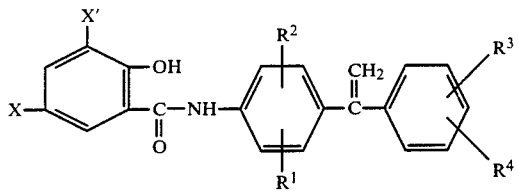

in which:

X and X' are, each, halo; and, $R^1$, $R^2$, $R^3$ and $R^4$ are, each, hydrogen, methyl or halo.

The term "halo" is used to include chloro, fluoro, iodo and bromo. Also included in this invention are the O-$C_{2-6}$-alkanoyl derivatives of the compounds of formula I such as at the 2-hydroxy group of the structures of formula I.

A subgeneric group of the compounds of formula I are those in which $R^1$, $R^2$ and $R^3$ are hydrogen and $R^4$ is halo. X and X' are, preferably, either iodo or bromo at both position.

The compounds of formula I are prepared by condensing a selected halosalicylic acid with an optionally substituted 1-(4-aminophenyl)-1-phenylethylene in the presence of an amide forming reagent as known to the art. Especially useful are the halo condensing agents such as phosphorus trichloride, phosphorus oxychloride, thionyl chloride or phosphorus pentachloride. The reactants are dissolved in a suitable inert organic solvent at from ambient to reflux temperature until the reaction is complete. Usually, the reaction is run at reflux in chlorobenzene for from 1-4 hours. The desired product of formula I is isolated using standard chemical isolation methods.

The starting materials for the described reaction are available in the art. Halo substituted salicylic acids are commercially available. The 1-(4-aminophenyl)-1-phenylethylenes are prepared either by the method of H. Hart et al., J. Org. Chem. 27 116 (1962) which involves dehydration of the corresponding carbinol, for example, using alcoholic hydrogen chloride, or by a Wittig reaction on the substituted benzophenone as reported in U.S. Pat. No. 4,435,418.

The compounds of this invention have general anthelmintic activity against parasites living in the digestive tract of various mammalian hosts such as swine, cattle, dogs, goats, horses, sheep or cats. Examples of these parasites are the nematodes, such as round worms, hookworms or pinworms, the cestodes, such as the tapeworms, and, especially, the flukes such as Fasciola hepatica. Flukicidal activity is often more pronounced than is anti-nematodal activity. The anthelmintic activity is observed following oral administration of a tablet, drench, bolus or other pharmaceutical, animal feed or veterinary composition which is adapted for oral administration.

For example, the disclosed compounds are generally effective in clearing mice of worm infections for laboratory purposes such as, among others, Syphacia obvelata and Aspicularis tetraptera (mouse pinworm), Nematospiroides dubius (mouse hookworm) and the migratory stages of Ascaris suum.

Other susceptible helminths include Toxocara canis, found in naturally infested dogs. Also, parasitic to this host are Ancylostoma canium, Trichuris vulpis (whipworm) and Physalaptera ssp.

Among the gastrointestinal parasites in sheep and cattle which are susceptible are Haemonchus contortus, Ostertagia spp., Trichostrongylus spp., Nematodirus spp., Trichuris ovis, Cooperia spp., Strongyloides papillosus, Bunostomum spp., Chabertia sp. and Oesophagostomum spp.

In practice, the phenylethenylphenyl-2-hydroxybenzamide active ingredient is formulated with a nontoxic pharmaceutical, veterinary or feed carrier therefor to give the anthelmintic compositions of this invention. The carrier may be a standard animal feed composition which is based on a feed premix whole feed composition or an orally ingestible anthelmintic carrier for the active ingredient, for example, a drench, a dispersible tablet or powder, or a gelatin capsule. It may also be a pharmaceutically acceptable diluent or excipient of the kind normally used in the production of veterinary or human medicaments, for example, maize, starch, terra alba, lactose, sucrose, calcium phosphate, gelatin, talcum, stearic acid, magnesium stearate, dextrin, agar, pectin or acacia.

Exemplary of liquid carriers are peanut oil, olive oil, sesame oil and water. Similarly, the carrier or diluent may include a time delay capability such as using resins or waxes. Various bolus preparations are especially useful for ruminant domesticated animals.

The compositions are advantageously made up in a dosage unit form adapted for the desired frequency and mode of administration. Thus, for the preferred oral administration, the dosage unit may take the form of a suspension, top dressing, tablet, packaged powder, bolus or encapsulated dispersible powder. The quantity of active ingredient in each dosage unit will be such that one or more units are required for each therapeutic administration.

Where tableting is used, the resulting tablets may be coated with methyl methacrylate to form an enteric coating, i.e., a coating which is substantially insoluble in gastric secretion but substantially soluble in intestinal fluids.

The compositions, thusly prepared using an anthelmintic, but nontoxic, quantity of a compound of formula I chosen from the range of 5–30 mg/kg., are administered orally to an infected or susceptible host for curative or prophylactic anthelmintic activity. Preferably, one clearing dose is used but one or two further doses may be necessary for severe infections.

As an example of the activity of these new compounds, N-[4-(1-phenylethenyl)phenyl]-2-hydroxy-3,5-diiodobenzamide at a dosage level of 10 mg/kg, administered intra-ruminally, reduced F. hepatica in sheep 69%; abomasal nematodes (H. contortus and N. spathiger), 24%.

The following examples illustrate specific aspects of the invention which may be employed in preparing and using the compositions of the invention but are not intended to limit the scope of the invention described. Degrees of temperature are in Centigrade unless otherwise noted.

EXAMPLE 1

| Typical Cattle Bolus | |
| --- | --- |
| N—[4-(1-phenylethenyl)phenyl]-2-hydroxy-3,5-diiodobenzamide | 1.5 grams |
| Calcium phosphate | 2.5 grams |
| Maize Starch | 0.54 grams |
| Talcum | 0.14 grams |
| Gum Arabic | 0.15 grams |
| Magnesium Stearate | 0.5 grams |

The calcium phosphate and the anthelmintic compound are thoroughly mixed, and the mixture reduced to a particle size finer than 60 mesh. About one-half of the starch is added, as an aqueous paste, and the resulting mixture granulated. The granules are passed through a No. 10 mesh screen and dried at 110°–130° F. for about eight hours. The dried materials are then passed through a No. 16 mesh screen. The guar gum and the balance of the starch are added and the mixture thoroughly blended. Finally, the remainder of the ingredients are added and the entire mass thoroughly mixed and compressed into a bolus. The magnesium stearate, talcum and gum acacia are of a particle size to pass a No. 10 mesh screen.

The bolus is administered to field cattle orally using a bolus gun.

EXAMPLE 2

A mixture of 400 ml of ethyl ether containing 0.5 mole of 4-chlorophenylmagnesium bromide was added over 1 hour to a mixture of 13.5 g of 4-aminoacetophenone in 500 ml of ether under nitrogen. After heating at reflux for 3 hours, the cooled mixture was quenched with 250 ml of saturated ammonium chloride solution. The dried ethereal layer was evaporated. The residual oil was mixed with 250 ml of 3N hydrochloric acid. After heating on the steam bath for 3 hours, the cooled mixture was separated from a soft solid. The product was taken up in 100 ml of ethanol. Ether (600 ml) was added to give a solid, 14.3 g of 1-(4-aminophenyl)-1-phenylethylene hydrochloride, m.p. 181°–183°.

A mixture of 5.06 g (0.013 mole) of 3,5-diiodosalicylic acid and 3.5 g (0.013 mole) of the amine salt in 125 ml of chlorobenzene was heated at reflux. Phosphorus trichloride (1.5 ml) was added over 45 minutes. After heating at reflux for 2 hours, the mixture was cooled and stripped to give a residue. The solid was extracted with 250 ml of methylene chloride and filtered through a filter aid. The extract was washed, dried and evaporated. The residue, in methylene chloride, was passed over a silica gel column with a methylene chloride/n-hexane eluant to give 2.23 g of white solid; N-[4-[1-(4-chlorophenyl)-ethenyl]phenyl]-2-hydroxy-3,5-diiodobenzamide, m.p. 181°–184°.

Anal. Calcd. for $C_{21}H_{14}ClI_2NO_2$: C, 41.93; H, 2.35; N, 2.33. Found: C, 41.81; H, 2.71; N, 2.23.

EXAMPLE 3

Using the reaction conditions of Example 2, 5.92 g (0.02 mole) of 3,5-dibromosalicylic acid and 5.32 g (0.02 mole) of 1-(4-aminophenyl)-1-(4-chlorophenyl)ethylene in the presence of phosphorus trichloride were reacted to give 4.26 of purified N-[4-[1-(4-chlorophenyl)ethenyl]phenyl]-2-hydroxy-3,5-dibromobenzamide, m.p. 181°–183°.

Anal. Calcd. for $C_{21}H_{14}Br_2ClNO_2$: C, 49.69; H, 2.78; N, 2.76. Found: C, 50.26; H, 2.89; N, 2.78.

EXAMPLE 4

To 2.5 g (0.06 mole) of 60% commercial sodium hydride was added 50 ml of sieve-dried dimethylsulfoxide. The stirring mixture was heated until evolution of hydrogen gas ceased. The mixture was cooled in an ice-box and 21.4 g (0.06 mole) of (methyl)triphenylphosphonium bromide, a Wittig reagent, dissolved in 60 ml of sieve-dried dimethylsulfoxide, was added in a few minutes. The resulting mixture was stirred for 15 minutes at room temperature. Then, 9 g (0.03 mole) of 2,4'-dichloro-4-nitrobenzophenone was added as a solid. The resulting mixture was heated at 75°–80° under nitrogen overnight. The reaction mixture was diluted with 200 ml of water and extracted with ether. The ethereal extract was dried over magnesium sulfate. The extract was evaporated to dryness. The residue was dissolved in 30 ml of methylene chloride and the solution put through a silica gel column (5.5×21 cm) with an eluant of methylene chloride/n-hexane. The selected fractions were combined and evaporated to give 2.35 g of 1-(4-chlorophenyl)-1-(2-chloro-4-nitrophenyl)ethylene.

A stirring solution of 2.35 g (0.008 mole) of the nitro compound in 125 ml of ethanol was brought to boiling and 10 g of sodium sulfhydrate ($NaSH \cdot XH_2O$) in 30 ml of water was added during a 0.5 hour period. After 24 ml (8 g) of the reducing mixture had been added, thin layer chromatography (TLC) (silica gel plate, 1:1 methylene chloride/n-hexane) demonstrated disappearance of the starting material. The mixture was concentrated to 50 ml and poured into 200 ml of water at which point an oil separated. The aqueous phase was decanted and its oil was taken up in ether. The extract was washed with water and dried. The ether extract was evaporated. The resulting oil was treated with 10 ml of 6N hydrochloric acid to give 2.45 g of a tan colored solid. Recrystallization from isopropanol gave 1.01 g of purified 1-(4-amino-2-chlorophenyl)-1-(4-chlorophenyl)ethylene as the hydrochloride.

A second run gave 2.92 g of the same product.

To a stirring solution of 4.13 g (0.01 mol) 3,5-diiodosalicylic acid and 2.63 (0.01 mole) of the ethylene compound in 100 ml of chlorobenzene at reflux was added 1.5 ml of phosphorus trichloride over a 2 hour period. Thin layer chromatography (8:1:1 methylene chloride/ether/acetic acid on a silica gel plate) demonstrated the absence of starting material. The reaction mixture was evaporated to a syrup and redissolved in 50 ml of methylene chloride. The extract was washed with water and dried. Evaporation of solvent and trituration of the residue with n-hexane gave 5.36 g (79.5%) of N-[3-chloro-4-(1-(4-chlorophenyl)ethenyl)phenyl]-2-hydroxy-3,5-diiodobenzamide as an off-white solid. Further purification of a small sample from aqueous ethanol gave an analytical sample, m.p. 171°–175° (capillary).

Anal. Calcd. for $C_{21}H_{13}I_2Cl_2NO_2$: C, 39.66; H, 2.06; N, 2.20. Found: C, 39.68; H, 2.17; N, 2.04.

EXAMPLE 5

To a refluxing solution of 7.9 g (0.02 mole) of 3,5-diiodosalicylic acid and 4.6 g (0.02 mole) of 1-(4-aminophenyl)-1-phenylethylene in 125 ml of chlorobenzene was added 3 g (0.022 mole) of phosphorus trichloride over a 1 hour period. The resulting mixture was refluxed for 2 hours, cooled, diluted with 100 ml of methylene chloride. The organic phase was washed with 250 ml of water and dried. The extract was evaporated to dryness. After redissolving the residue in minimum amount of methylene chloride, the solution was flash-chromatographed on a silica gel column. The desired component was eluted with 2 liters of methylene chloride/n-hexane. Evaporation of its solvent gave 4.9 g of N-[4-(1-phenylethenyl)phenyl] -2-hydroxy-3,5-diiodobenzamide. Recrystallization from aqueous ethanol gave 4.2 g of purified product, m.p. 173°–174°.

EXAMPLE 6

Using the reaction sequence of Example 4, 3,5-diiodosalicylic acid is reacted with 1-(4-amino-2-chloro-6-methylphenyl)-1-(4-chlorophenyl)ethylene in the presence of phosphorus trichloride to give N-[3-chloro-5-methyl-4-[1-(4-chlorophenyl)ethenyl]phenyl]-3,5-diiodo-2-hydroxybenzamide. The benzophenone used as starting material for the Wittig reaction was prepared by reacting 4-chlorobenzyl cyanide with 3-chloro-5-methyl-1-nitrobenzene followed by oxidation with alkaline peroxide as known in the literature.

EXAMPLE 7

The reaction sequences of Examples 2-6 are used to prepare the following compounds of this invention:
N-[4-(1-phenylethenyl)phenyl]-2-hydroxy-3,5-difluorobenzamide.
N-[4-[1-(2-iodophenyl)ethenyl]phenyl]-2-hydroxy-3,5-dichlorobenzamide.
N-[4-[1-(2,4-dichlorophenyl)ethenyl]-2-iodophenyl]-2-hydroxy-3,5-diiodobenzamide.

What is claimed is:

1. An anthelmintic composition for internal administration comprising an anthelmintic but nontoxic quantity of a compound of the formula:

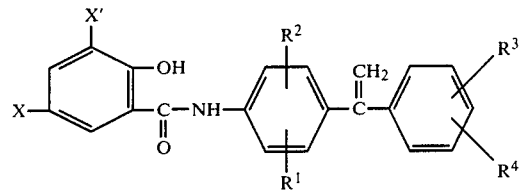

in which:
X and X' are, each, halo; and
$R^1$, $R^2$, $R^3$ and $R^4$ are, each, hydrogen, methyl or halo, or an O-$C_{2-6}$-alkanoyl derivative thereof, combined with a pharmaceutical, animal feed or veterinary carrier.

2. The composition of claim 1 in which the compound is N-[4-(1-phenylethenyl)phenyl]-3,5-diiodo-2-hydroxybenzamide.

3. The composition of claim 1 in which the compound is N-[3-chloro-4-[1-(4-chlorophenyl)ethenyl]phenyl]-3,5-diiodo-2-hydroxybenzamide.

4. The composition of claim 1 in which the compound is N-[4-[1-(4-chlorophenyl)ethenyl]phenyl]-3,5-diiodo-2-hydroxybenzamide.

5. The composition of claim 1 in which the compound is N-[4-[1-(4-chlorophenyl)ethenyl]phenyl]-3,5-dibromo-2-hydroxybenzamide.

6. The composition of claim 1 in which the composition is a ruminant bolus for oral administration.

7. A chemical compund of the formula:

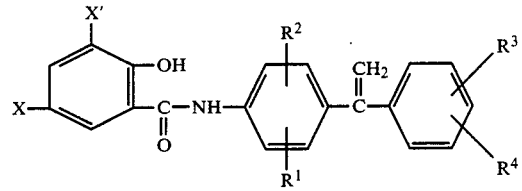

in which:
X and X' are, each, halo; and
$R^1$, $R^2$, $R^3$ and $R^4$ are, each, hydrogen, methyl or halo, or an O-$C_{2-6}$-alkanoyl derivative thereof.

8. The compound of claim 7 in which:
X and X' are, both, bromo or iodo;
$R^1$, $R^2$ and $R^3$ are hydrogen; and
$R^4$ is halo.

9. The compound of claim 7 being N-[4-(1-phenylethenyl)phenyl]-3,5-diiodo-2-hydroxybenzamide.

10. The compound of claim 7 being N-[3-chloro-4-[1-(4-chlorophenyl)-ethenyl]phenyl]-3,5-diiodo-2-hydroxybenzamide.

11. The compound of claim 7 being N-[4-[1-(4-chlorophenyl)ethenyl]phenyl]-3,5-diiodo-2-hydroxybenzamide.

12. The compound of claim 7 being N-[4-[1-(4-chlorophenyl)ethenyl]phenyl]-3,5-dibromo-2-hydroxybenzamide.

* * * * *